US009076431B2

(12) United States Patent
Kamath et al.

(10) Patent No.: US 9,076,431 B2
(45) Date of Patent: Jul. 7, 2015

(54) FILTER ARCHITECTURE FOR AN ADAPTIVE NOISE CANCELER IN A PERSONAL AUDIO DEVICE

(75) Inventors: Gautham Devendra Kamath, Austin, TX (US); Jon D. Hendrix, Wimberly, TX (US)

(73) Assignee: Cirrus Logic, Inc., Austin, TX (US)

( * ) Notice: Subject to any disclaimer, the term of this patent is extended or adjusted under 35 U.S.C. 154(b) by 754 days.

(21) Appl. No.: 13/436,828

(22) Filed: Mar. 30, 2012

(65) Prior Publication Data

US 2012/0308026 A1 Dec. 6, 2012

Related U.S. Application Data

(60) Provisional application No. 61/493,162, filed on Jun. 3, 2011.

(51) Int. Cl.
*A61F 11/06* (2006.01)
*G10K 11/16* (2006.01)
(Continued)

(52) U.S. Cl.
CPC ...... *G10K 11/1784* (2013.01); *G10K 2210/108* (2013.01); *G10K 2210/3017* (2013.01);
(Continued)

(58) Field of Classification Search
CPC ............ G10K 11/1784; G10K 11/178; G10K 2210/108; G10K 2210/3028; G10K 2210/3045
USPC ................... 381/71.11, 71.1, 71.6, 71.8, 94.7
See application file for complete search history.

(56) References Cited

U.S. PATENT DOCUMENTS 5,251,263 A 10/1993 Andrea et al.
5,278,913 A 1/1994 Delfosse et al.
(Continued)

FOREIGN PATENT DOCUMENTS

DE 102011013343 A1 9/2012
EP 1880699 A2 1/2008
(Continued)

OTHER PUBLICATIONS

Parkins, et al., "Narrowband and broadband active control in an enclosure using the acoustic energy density", J. Acoust. Soc. Am. Jul. 2000, pp. 192-203, vol. 108, issue 1, US.
(Continued)

*Primary Examiner* — Vivian Chin
*Assistant Examiner* — Douglas Suthers
(74) *Attorney, Agent, or Firm* — Mitch Harris, Atty at Law, LLC; Andrew M. Harris

(57) ABSTRACT

A personal audio device, such as a wireless telephone, includes an adaptive noise canceling (ANC) circuit that generates an anti-noise signal from a reference microphone signal and injects the anti-noise signal into the speaker or other transducer output to cancel ambient audio sounds. A processing circuit implements one or more adaptive filters that control the generation of the anti-noise signal. At least one of the adaptive filters is partitioned into a first portion having a fixed frequency response and a second portion having a variable frequency response. The partitioned filter may be an adaptive filter that generates the anti-noise signal directly from the reference microphone signal. An error microphone may be provided to measure the ambient sounds and transducer output near the transducer, and a secondary path adaptive filter included to generate an error signal from the error microphone signal, which may be partitioned, alone or in combination.

36 Claims, 6 Drawing Sheets

(51) Int. Cl.
*H03B 29/00* (2006.01)
*H03B 15/00* (2006.01)
*G10K 11/178* (2006.01)

(52) U.S. Cl.
CPC .................. *G10K2210/3028* (2013.01); *G10K 2210/30391* (2013.01); *G10K 2210/3045* (2013.01); *G10K 2210/503* (2013.01)

(56) References Cited

U.S. PATENT DOCUMENTS

| | | | |
|---|---|---|---|
| 5,337,365 | A | 8/1994 | Hamabe et al. |
| 5,410,605 | A | 4/1995 | Sawada et al. |
| 5,425,105 | A | 6/1995 | Lo et al. |
| 5,586,190 | A | 12/1996 | Trantow et al. |
| 5,640,450 | A | 6/1997 | Watanabe |
| 5,699,437 | A | 12/1997 | Finn |
| 5,706,344 | A | 1/1998 | Finn |
| 5,768,124 | A | 6/1998 | Stothers et al. |
| 5,815,582 | A | 9/1998 | Claybaugh et al. |
| 5,946,391 | A | 8/1999 | Dragwidge et al. |
| 5,991,418 | A | 11/1999 | Kuo |
| 6,041,126 | A | 3/2000 | Terai et al. |
| 6,118,878 | A | 9/2000 | Jones |
| 6,219,427 | B1 | 4/2001 | Kates et al. |
| 6,418,228 | B1 | 7/2002 | Terai et al. |
| 6,434,246 | B1 | 8/2002 | Kates et al. |
| 6,434,247 | B1 | 8/2002 | Kates et al. |
| 6,768,795 | B2 | 7/2004 | Feltstrom et al. |
| 6,850,617 | B1 | 2/2005 | Weigand |
| 7,058,463 | B1 | 6/2006 | Ruha et al. |
| 7,103,188 | B1 | 9/2006 | Jones |
| 7,181,030 | B2 | 2/2007 | Rasmussen et al. |
| 7,330,739 | B2 | 2/2008 | Somayajula |
| 7,365,669 | B1 | 4/2008 | Melanson |
| 7,742,790 | B2 | 6/2010 | Konchitsky et al. |
| 8,019,050 | B2 | 9/2011 | Mactavish et al. |
| 8,249,262 | B2 | 8/2012 | Chua et al. |
| 8,290,537 | B2 | 10/2012 | Lee et al. |
| 8,379,884 | B2 | 2/2013 | Horibe et al. |
| 8,401,200 | B2 | 3/2013 | Tiscareno et al. |
| 2001/0053228 | A1 | 12/2001 | Jones |
| 2002/0003887 | A1 | 1/2002 | Zhang et al. |
| 2004/0165736 | A1 | 8/2004 | Hetherington et al. |
| 2004/0167777 | A1 | 8/2004 | Hetherington et al. |
| 2004/0264706 | A1 | 12/2004 | Ray et al. |
| 2005/0117754 | A1 | 6/2005 | Sakawaki |
| 2005/0240401 | A1 | 10/2005 | Ebenezer |
| 2006/0153400 | A1 | 7/2006 | Fujita et al. |
| 2007/0030989 | A1 | 2/2007 | Kates |
| 2007/0033029 | A1 | 2/2007 | Sakawaki |
| 2007/0038441 | A1 | 2/2007 | Inoue et al. |
| 2007/0053524 | A1 | 3/2007 | Haulick et al. |
| 2007/0076896 | A1 | 4/2007 | Hosaka et al. |
| 2007/0154031 | A1 | 7/2007 | Avendano et al. |
| 2007/0258597 | A1 | 11/2007 | Rasmussen et al. |
| 2007/0297620 | A1 | 12/2007 | Choy |
| 2008/0019548 | A1 | 1/2008 | Avendano |
| 2008/0181422 | A1 | 7/2008 | Christoph |
| 2008/0226098 | A1 | 9/2008 | Haulick et al. |
| 2009/0012783 | A1 | 1/2009 | Klein |
| 2009/0034748 | A1 | 2/2009 | Sibbald |
| 2009/0041260 | A1 | 2/2009 | Jorgensen et al. |
| 2009/0046867 | A1 | 2/2009 | Clemow |
| 2009/0196429 | A1 | 8/2009 | Ramakrishnan et al. |
| 2009/0220107 | A1 | 9/2009 | Every et al. |
| 2009/0238369 | A1 | 9/2009 | Ramakrishnan et al. |
| 2009/0245529 | A1 | 10/2009 | Asada et al. |
| 2009/0254340 | A1 | 10/2009 | Sun et al. |
| 2009/0290718 | A1 | 11/2009 | Kahn et al. |
| 2009/0296965 | A1 | 12/2009 | Kojima |
| 2009/0304200 | A1 | 12/2009 | Kim et al. |
| 2010/0014683 | A1 | 1/2010 | Maeda et al. |
| 2010/0014685 | A1 | 1/2010 | Wurm |
| 2010/0061564 | A1 | 3/2010 | Clemow et al. |
| 2010/0069114 | A1 | 3/2010 | Lee et al. |
| 2010/0082339 | A1 | 4/2010 | Konchitsky et al. |
| 2010/0098263 | A1 | 4/2010 | Pan et al. |
| 2010/0124336 | A1 | 5/2010 | Shridhar et al. |
| 2010/0166203 | A1 | 7/2010 | Peissig et al. |
| 2010/0195838 | A1 | 8/2010 | Bright |
| 2010/0195844 | A1 | 8/2010 | Christoph et al. |
| 2010/0272276 | A1 | 10/2010 | Carreras et al. |
| 2010/0272283 | A1 | 10/2010 | Carreras et al. |
| 2010/0274564 | A1 | 10/2010 | Bakalos et al. |
| 2010/0296666 | A1 | 11/2010 | Lin |
| 2010/0296668 | A1 | 11/2010 | Lee et al. |
| 2010/0310086 | A1 | 12/2010 | Magrath et al. |
| 2010/0322430 | A1 | 12/2010 | Isberg |
| 2011/0007907 | A1 | 1/2011 | Park et al. |
| 2011/0106533 | A1 | 5/2011 | Yu |
| 2011/0142247 | A1 | 6/2011 | Fellers et al. |
| 2011/0144984 | A1 | 6/2011 | Konchitsky |
| 2011/0158419 | A1 | 6/2011 | Theverapperuma et al. |
| 2011/0222698 | A1 | 9/2011 | Asao et al. |
| 2011/0249826 | A1 | 10/2011 | Van Leest |
| 2011/0288860 | A1 | 11/2011 | Schevciw et al. |
| 2011/0293103 | A1 | 12/2011 | Park et al. |
| 2011/0299695 | A1 | 12/2011 | Nicholson |
| 2011/0317848 | A1 | 12/2011 | Ivanov et al. |
| 2012/0135787 | A1 | 5/2012 | Kusunoki et al. |
| 2012/0140943 | A1 | 6/2012 | Hendrix et al. |
| 2012/0170766 | A1 | 7/2012 | Alves et al. |
| 2012/0207317 | A1 | 8/2012 | Abdollahzadeh Milani et al. |
| 2012/0250873 | A1* | 10/2012 | Bakalos et al. .............. 381/71.6 |
| 2012/0259626 | A1 | 10/2012 | Li et al. |
| 2012/0300958 | A1 | 11/2012 | Klemmensen |
| 2012/0308021 | A1 | 12/2012 | Kwatra et al. |
| 2012/0308024 | A1 | 12/2012 | Alderson et al. |
| 2012/0308025 | A1 | 12/2012 | Hendrix et al. |
| 2012/0308027 | A1 | 12/2012 | Kwatra |
| 2012/0308028 | A1 | 12/2012 | Kwatra et al. |
| 2012/0310640 | A1 | 12/2012 | Kwatra et al. |
| 2013/0010982 | A1 | 1/2013 | Elko et al. |
| 2013/0243225 | A1 | 9/2013 | Yokota |
| 2013/0272539 | A1 | 10/2013 | Kim et al. |
| 2013/0287218 | A1 | 10/2013 | Alderson et al. |
| 2013/0287219 | A1 | 10/2013 | Hendrix et al. |
| 2013/0301842 | A1 | 11/2013 | Hendrix et al. |
| 2013/0301846 | A1 | 11/2013 | Alderson et al. |
| 2013/0301847 | A1 | 11/2013 | Alderson et al. |
| 2013/0301848 | A1 | 11/2013 | Zhou et al. |
| 2013/0301849 | A1 | 11/2013 | Alderson et al. |
| 2013/0343556 | A1 | 12/2013 | Bright |
| 2013/0343571 | A1 | 12/2013 | Rayala et al. |
| 2014/0044275 | A1 | 2/2014 | Goldstein et al. |
| 2014/0050332 | A1 | 2/2014 | Nielsen et al. |
| 2014/0086425 | A1 | 3/2014 | Jensen et al. |
| 2014/0177851 | A1 | 6/2014 | Kitazawa et al. |
| 2014/0211953 | A1 | 7/2014 | Alderson et al. |
| 2014/0270222 | A1 | 9/2014 | Hendrix et al. |
| 2014/0270223 | A1 | 9/2014 | Li et al. |
| 2014/0270224 | A1 | 9/2014 | Zhou et al. |

FOREIGN PATENT DOCUMENTS

| | | | |
|---|---|---|---|
| EP | 1947642 | A1 | 7/2008 |
| EP | 2133866 | A1 | 12/2009 |
| EP | 2216774 | A1 | 8/2010 |
| EP | 2395500 | A1 | 12/2011 |
| EP | 2395501 | A1 | 12/2011 |
| GB | 2401744 | A | 11/2004 |
| GB | 2455821 | A | 6/2009 |
| GB | 2455824 | A | 6/2009 |
| GB | 2455828 | A | 6/2009 |
| GB | 2484722 | A | 4/2012 |
| JP | H06-186985 | A | 7/1994 |
| WO | WO 03/015074 | A1 | 2/2003 |
| WO | WO 2004009007 | A1 | 1/2004 |
| WO | WO 2007007916 | A1 | 1/2007 |
| WO | WO 2007113487 | A1 | 11/2007 |

(56) References Cited

FOREIGN PATENT DOCUMENTS

WO WO 2010117714 A1 10/2010
WO WO 2012/134874 A1 10/2012

OTHER PUBLICATIONS

Feng, et al.., "A broadband self-tuning active noise equaliser", Signal Processing, Oct. 1, 1997, pp. 251-256, vol. 62, No. 2, Elsevier Science Publishers B.V. Amsterdam, NL.
Zhang, et al., "A Robust Online Secondary Path Modeling Method with Auxiliary Noise Power Scheduling Strategy and Norm Constraint Manipulation", IEEE Transactions on Speech and Audio Processing, IEEE Service Center, Jan. 1, 2003, pp. 45-53, vol. 11, No. 1, NY.
Lopez-Gaudana, et al., "A hybrid active noise cancelling with secondary path modeling", 51st Midwest Symposium on Circuits and Systems, MWSCAS 2008, Aug. 10-13, 2008, pp. 277-280, IEEE, Knoxville, TN.
International Search Report and Written Opinion in PCT/US2012/037452, mailed on Apr. 4, 2013, 14 pages. (pp. 1-14 in pdf).
Written Opinion of the International Preliminary Examining Authority in PCT/US2012/037452, mailed on Aug. 29, 2013, 7 pages (pp. 1-7 in pdf).
International Preliminary Report on Patentability in PCT/US2012/037452, mailed on Nov. 29, 2013, 27 pages (pp. 1-27 in pdf).
U.S. Appl. No. 13/968,007, filed Aug. 15, 2013, Hendrix, et al.
Black, John W., "An Application of Side-Tone in Subjective Tests of Microphones and Headsets", Project Report No. NM 001 064.01.20, Research Report of the U.S. Naval School of Aviation Medicine, Feb. 1, 1954, 12 pages (pp. 1-12 in pdf), Pensacola, FL, US.
Peters, Robert W., "The Effect of High-Pass and Low-Pass Filtering of Side-Tone Upon Speaker Intelligibility", Project Report No. NM 001 064.01.25, Research Report of the U.S. Naval School of Aviation Medicine, Aug. 16, 1954, 13 pages (pp. 1-13 in pdf), Pensacola, FL, US.
U.S. Appl. No. 14/197,814, filed Mar. 5, 2014, Kaller, et al.
U.S. Appl. No. 14/210,537, filed Mar. 14, 2014, Abdollahzadeh Milani, et al.
U.S. Appl. No. 14/210,589, filed Mar. 14, 2014, Abdollahzadeh Milani, et al.
Lane, et al., "Voice Level: Autophonic Scale, Perceived Loudness, and the Effects of Sidetone", The Journal of the Acoustical Society of America, Feb. 1961, pp. 160-167, vol. 33, No. 2., Cambridge, MA, US.
Liu, et al., "Compensatory Responses to Loudness-shifted Voice Feedback During Production of Mandarin Speech", Journal of the Acoustical Society of America, Oct. 2007, pp. 2405-2412, vol. 122, No. 4.
Paepcke, et al., "Yelling in the Hall: Using Sidetone to Address a Problem with Mobile Remote Presence Systems", Symposium on User Interface Software and Technology, Oct. 10-19, 2011, 10 pages (pp. 1-10 in pdf), Santa Barbara, CA, US.
Therrien, et al., "Sensory Attenuation of Self-Produced Feedback: The Lombard Effect Revisited", PLOS One, Nov. 2012, pp. 1-7, vol. 7, Issue 11, e49370, Ontario, Canada.
U.S. Appl. No. 13/686,353, filed Nov. 27, 2012, Hendrix, et al.
U.S. Appl. No. 13/795,160, filed Mar. 12, 2013, Hendrix, et al.
U.S. Appl. No. 13/692,367, filed Dec. 3, 2012, Alderson, et al.
U.S. Appl. No. 13/722,119, filed Dec. 3, 2012, Hendrix, et al.
U.S. Appl. No. 13/727,718, filed Dec. 27, 2012, Alderson, et al.
U.S. Appl. No. 13/784,018, filed Mar. 4, 2013, Alderson, et al.
U.S. Appl. No. 13/787,906, filed Mar. 7, 2013, Alderson, et al.
U.S. Appl. No. 13/729,141, filed Dec. 28, 2012, Zhou, et al.
U.S. Appl. No. 13/794,931, filed Mar. 12, 2013, Lu, et al.
U.S. Appl. No. 13/794,979, filed Mar. 12, 2013, Alderson, et al.
Toochinda, et al. "A Single-Input Two-Output Feedback Formulation for ANC Problems," Proceedings of the 2001 American Control Conference, Jun. 2001, pp. 923-928, vol. 2, Arlington, VA.
Johns, et al., "Continuous-Time LMS Adaptive Recursive Filters," IEEE Transactions on Circuits and Systems, Jul. 1991, pp. 769-778, vol. 38, No. 7, IEEE Press, Piscataway, NJ.
Shoval, et al., "Comparison of DC Offset Effects in Four LMS Adaptive Algorithms," IEEE Transactions on Circuits and Systems II: Analog and Digital Processing, Mar. 1995, pp. 176-185, vol. 42, Issue 3, IEEE Press, Piscataway, NJ.
Mali, Dilip, "Comparison of DC Offset Effects on LMS Algorithm and its Derivatives," International Journal of Recent Trends in Engineering, May 2009, pp. 323-328, vol. 1, No. 1, Academy Publisher.
Kates, James M., "Principles of Digital Dynamic Range Compression," Trends in Amplification, Spring 2005, pp. 45-76, vol. 9, No. 2, Sage Publications.
Gao, et al., "Adaptive Linearization of a Loudspeaker," IEEE International Conference on Acoustics, Speech, and Signal Processing, Apr. 14-17, 1991, pp. 3589-3592, Toronto, Ontario, CA.
Akhtar, et al., "A Method for Online Secondary Path Modeling in Active Noise Control Systems," IEEE International Symposium on Circuits and Systems, May 23-26, 2005, pp. 264-267, vol. 1, Kobe, Japan.
Davari, et al., "A New Online Secondary Path Modeling Method for Feedforward Active Noise Control Systems," IEEE International Conference on Industrial Technology, Apr. 21-24, 2008, pp. 1-6, Chengdu, China.
Lan, et al., "An Active Noise Control System Using Online Secondary Path Modeling With Reduced Auxiliary Noise," IEEE Signal Processing Letters, Jan. 2002, pp. 16-18, vol. 9, Issue 1, IEEE Press, Piscataway, NJ.
Liu, et al., "Analysis of Online Secondary Path Modeling With Auxiliary Noise Scaled by Residual Noise Signal," IEEE Transactions on Audio, Speech and Language Processing, Nov. 2010, pp. 1978-1993, vol. 18, Issue 8, IEEE Press, Piscataway, NJ.
U.S. Appl. No. 14/029,159, filed Sep. 17, 2013, Li, et al.
U.S. Appl. No. 14/062,951, filed Oct. 25, 2013, Zhou, et al.
Pfann, et al., "LMS Adaptive Filtering with Delta-Sigma Modulated Input Signals," IEEE Signal Processing Letters, Apr. 1998, pp. 95-97, vol. 5, No. 4, IEEE Press, Piscataway, NJ.
Kuo, et al., "Active Noise Control: A Tutorial Review," Proceedings of the IEEE, Jun. 1999, pp. 943-973, vol. 87, No. 6, IEEE Press, Piscataway, NJ.
Silva, et al., "Convex Combination of Adaptive Filters With Different Tracking Capabilities," IEEE International Conference on Acoustics, Speech, and Signal Processing, Apr. 15-20, 2007, pp. III 925-928, vol. 3, Honolulu, HI, USA.
Abdollahzadeh Milani, et al., "On Maximum Achievable Noise Reduction in ANC Systems",2010 IEEE International Conference on Acoustics Speech and Signal Processing, Mar. 14-19, 2010, pp. 349-352, Dallas, TX, US.
U.S. Appl. No. 14/228,322, filed Mar. 28, 2014, Alderson, et al.
U.S. Appl. No. 13/762,504, filed Feb. 8, 2013, Abdollahzadeh Milani, et al.
U.S. Appl. No. 13/721,832, filed Dec. 20, 2012, Lu, et al.
U.S. Appl. No. 13/724,656, filed Dec. 21, 2012, Lu, et al.
U.S. Appl. No. 14/252,235, filed Apr. 14, 2014, Lu, et al.
U.S. Appl. No. 13/968,013, filed Aug. 15, 2013, Abdollahzadeh Milani, et al.
U.S. Appl. No. 13/924,935, filed Jun. 24, 2013, Hellman.
U.S. Appl. No. 13/896,526, filed May 17, 2013, Naderi.
U.S. Appl. No. 14/101,955, filed Dec. 10, 2013, Alderson.
U.S. Appl. No. 14/101,777, filed Dec. 10, 2013, Alderson, et al.
Cohen, Israel, "Noise Spectrum Estimation in Adverse Environments: Improved Minima Controlled Recursive Averaging", IEEE Transactions on Speech and Audio Processing, Sep. 2003, pp. 1-11, vol. 11, Issue 5, Piscataway, NJ, US.
Ryan, et al., "Optimum Near-Field Performance of Microphone Arrays Subject to a Far-Field Beampattern Constraint", J. Acoust. Soc. Am., Nov. 2000, pp. 2248-2255, 108 (5), Pt. 1, Ottawa, Ontario, Canada.
Cohen, et al., "Noise Estimation by Minima Controlled Recursive Averaging for Robust Speech Enhancement", IEEE Signal Processing Letters, Jan. 2002, pp. 12-15, vol. 9, No. 1, Piscataway, NJ, US.

(56) References Cited

OTHER PUBLICATIONS

Martin, Rainer, "Noise Power Spectral Density Estimation Based on Optimal Smoothing and Minimum Statistics", IEEE Transactions on Speech and Audio Processing, Jul. 2001, pp. 504-512, vol. 9, No. 5, Piscataway, NJ, US.

Martin, Rainer, "Spectral Subtraction Based on Minimum Statistics", Signal Processing VII Theories and Applications, Proceedings of EUSIPCO-94, 7th European Signal Processing Conference, Sep. 13-16, 1994, pp. 1182-1185, vol. III, Edinburgh, Scotland, U.K.

Booij, et al., "Virtual sensors for local, three dimensional, broadband multiple-channel active noise control and the effects on the quiet zones", Proceedings of the International Conference on Noise and Vibration Engineering, ISMA 2010, Sep. 20-22, 2010, pp. 151-166, Leuven.

Kuo, et al., "Residual noise shaping technique for active noise control systems", J. Acoust. Soc. Am. 95 (3), Mar. 1994, pp. 1665-1668.

Lopez-Caudana, Edgar Omar, "Active Noise Cancellation: The Unwanted Signal and the Hybrid Solution", Adaptive Filtering Applications, Dr. Lino Garcia (Ed.), Jul. 2011, pp. 49-84, ISBN: 978-953-307-306-4, InTech.

Senderowicz, et al., "Low-Voltage Double-Sampled Delta-Sigma Converters", IEEE Journal on Solid-State Circuits, Dec. 1997, pp. 1907-1919, vol. 32, No. 12, Piscataway, NJ.

Hurst, et al., "An improved double sampling scheme for switched-capacitor delta-sigma modulators", 1992 IEEE Int. Symp. on Circuits and Systems, May 10-13, 1992, vol. 3, pp. 1179-1182, San Diego, CA.

Campbell, Mikey, "Apple looking into self-adjusting earbud headphones with noise cancellation tech", Apple Insider, Jul. 4, 2013, pp. 1-10 (10 pages in pdf), downloaded on May 14, 2014 from http://appleinsider.com/articles/13/07/04/apple-looking-into-self-adjusting-earbud-headphones-with-noisecancellation-tech.

Jin, et al. "A simultaneous equation method-based online secondary path modeling algorithm for active noise control", Journal of Sound and Vibration, Apr. 25, 2007, pp. 455-474, vol. 303, No. 3-5, London, GB.

Erkelens, et al., "Tracking of Nonstationary Noise Based on Data-Driven Recursive Noise Power Estimation", IEEE Transactions on Audio Speech and Language Processing, Aug. 2008, pp. 1112-1123, vol. 16, No. 6, Piscataway, NJ, US.

Rao, et al., "A Novel Two State Single Channel Speech Enhancement Technique", India Conference (INDICON) 2011 Annual IEEE, IEEE, Dec. 2011, 6 pages (pp. 1-6 in pdf), Piscataway, NJ, US.

Rangachari, et al., "A noise-estimation algorithm for highly non-stationary environments", Speech Communication, Feb. 2006, pp. 220-231, vol. 48, No. 2. Elsevier Science Publishers.

* cited by examiner

FILTER ARCHITECTURE FOR AN ADAPTIVE NOISE CANCELER IN A PERSONAL AUDIO DEVICE

This U.S. Patent Application Claims priority under 35 U.S.C. §119(e) to U.S. Provisional Patent Application Ser. No. 61/493,162 filed on Jun. 3, 2011.

BACKGROUND OF THE INVENTION

1. Field of the Invention

The present invention relates generally to personal audio devices such as wireless telephones that include adaptive noise cancellation (ANC), and more specifically, to a filter architecture for implementing ANC in a personal audio device.

2. Background of the Invention

Wireless telephones, such as mobile/cellular telephones, cordless telephones, and other consumer audio devices, such as mp3 players, are in widespread use. Performance of such devices with respect to intelligibility can be improved by providing noise canceling using a microphone to measure ambient acoustic events and then using signal processing to insert an anti-noise signal into the output of the device to cancel the ambient acoustic events.

The acoustic environment around personal audio devices such as wireless telephones provides a challenge for the implementation of ANC. In particular, conditions such as nearby voice activity, wind, mechanical noise on the device housing or unstable operation of the ANC system typically requires reset of the adaptive filter that generates the noise-canceling (anti-noise) signal. Since resetting the adaptive results in no noise canceling until the adaptive filter re-adapts, any time an event occurs that disrupts the operation of the ANC system, cancellation of ambient noise is disrupted, as well.

Therefore, it would be desirable to provide a personal audio device, including a wireless telephone, that provides noise cancellation that provides adequate performance under dynamically changing operating conditions. It would further be desirable to provide a mechanism for resetting an ANC system that does not cause the total loss of noise canceling while the ANC system re-adapts.

SUMMARY OF THE INVENTION

The above stated objective of providing a personal audio device providing adequate noise cancellation performance in dynamically changing operating conditions and that does not cause total loss of the correct anti-noise signal when the adaptive filter is reset, is accomplished in a personal audio device, a method of operation, and an integrated circuit.

The personal audio device includes a housing, with a transducer mounted on the housing for reproducing an audio signal that includes both source audio for playback to a listener and an anti-noise signal for countering the effects of ambient audio sounds in an acoustic output of the transducer, which may include the integrated circuit to provide adaptive noise-canceling (ANC) functionality. The method is a method of operation of the personal audio device and integrated circuit. A reference microphone is mounted on the housing to provide a reference microphone signal indicative of the ambient audio sounds. The personal audio device further includes an ANC processing circuit within the housing for adaptively generating an anti-noise signal from the reference microphone signal using one or more adaptive filters, such that the anti-noise signal causes substantial cancellation of the ambient audio sounds.

At least one of the one or more adaptive filters is partitioned into a first filter portion having a fixed frequency response that is combined with a variable frequency response of a second filter portion. The partitioned filter may be the adaptive filter that filters the reference microphone signal to generate the anti-noise signal. An error microphone may be included for controlling the adaptation of the anti-noise signal to cancel the ambient audio sounds and for correcting for the electro-acoustic path from the output of the processing circuit through the transducer. A secondary path adaptive filter may be used to generate an error signal from the error microphone signal and the secondary path adaptive filter may be partitioned, alone or in combination with partitioning of the adaptive filter that filters the reference microphone signal to generate the anti-noise signal.

The foregoing and other objectives, features, and advantages of the invention will be apparent from the following, more particular, description of the preferred embodiment of the invention, as illustrated in the accompanying drawings.

DESCRIPTION OF ILLUSTRATIVE EMBODIMENT

The present invention encompasses noise canceling techniques and circuits that can be implemented in a personal audio device, such as a wireless telephone. The personal audio device includes an adaptive noise canceling (ANC) circuit that measures the ambient acoustic environment and generates an anti-noise signal that is injected in the speaker (or other transducer) output to cancel ambient acoustic events. A reference microphone is provided to measure the ambient acoustic environment and an error microphone may be included for controlling the adaptation of the anti-noise signal to cancel the ambient audio sounds and for correcting for the electro-acoustic path from the output of the processing circuit through the transducer. Under certain operating conditions, e.g., when the ambient environment is one that the ANC circuit cannot adapt to, one that overloads the reference microphone, or causes the ANC circuit to operate improperly or in an unstable/chaotic manner, the adaptive filter(s) implementing the ANC circuit must generally be reset. The present invention uses one or more partitioned filters having a fixed frequency response portion and a variable frequency response portion to implement the adaptive filters that control generation of the anti-noise signal. When the response of the partitioned filter is reset, the filter response is restored to a nominal response, or another response selected for recovery from the disruptive condition, providing an immediate anti-noise response that, while initially not adapted to the ambient audio condition, provides some degree of noise-cancellation while the ANC circuit re-adapts. Further, the partitioned filter configuration can provide increased stability, since only a portion of the filter adapts, the amount of deviation from a nominal response can be reduced. Leakage can also be introduced to provide a time-dependent restoration of the adaptive filter response to a nominal response, which provides further stability in operation.

Figure 1:
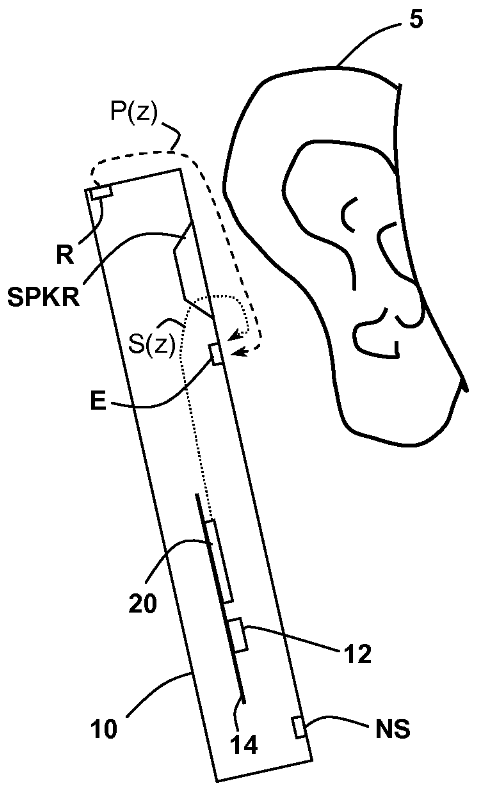
FIG. 1 is an illustration of a wireless telephone 10 in accordance with an embodiment of the present invention.

Referring now to FIG. 1, a wireless telephone 10 is illustrated in accordance with an embodiment of the present invention and is shown in proximity to a human ear 5. Illustrated wireless telephone 10 is an example of a device in which techniques in accordance with embodiments of the invention may be employed, but it is understood that not all of the elements or configurations embodied in illustrated wireless telephone 10, or in the circuits depicted in subsequent illustrations, are required in order to practice the invention recited in the Claims. Wireless telephone 10 includes a transducer, such as speaker SPKR that reproduces distant speech received by wireless telephone 10, along with other local audio events such as ringtones, stored audio program material, injection of near-end speech (i.e., the speech of the user of wireless telephone 10) to provide a balanced conversational perception, and other audio that requires reproduction by wireless telephone 10, such as sources from web-pages or other network communications received by wireless telephone 10 and audio indications, such as low battery and other system event notifications. A near-speech microphone NS is provided to capture near-end speech, which is transmitted from wireless telephone 10 to the other conversation participant(s).

Wireless telephone 10 includes adaptive noise canceling (ANC) circuits and features that inject an anti-noise signal into speaker SPKR to improve intelligibility of the distant speech and other audio reproduced by speaker SPKR. A reference microphone R is provided for measuring the ambient acoustic environment and is positioned away from the typical position of a user's mouth, so that the near-end speech is minimized in the signal produced by reference microphone R. A third microphone, error microphone E, is provided in order to further improve the ANC operation by providing a measure of the ambient audio combined with the audio reproduced by speaker SPKR close to ear 5, when wireless telephone 10 is in close proximity to ear 5. Exemplary circuit 14 within wireless telephone 10 includes an audio CODEC integrated circuit 20 that receives the signals from reference microphone R, near speech microphone NS and error microphone E and interfaces with other integrated circuits such as an RF integrated circuit 12 containing the wireless telephone transceiver. In other embodiments of the invention, the circuits and techniques disclosed herein may be incorporated in a single integrated circuit that contains control circuits and other functionality for implementing the entirety of the personal audio device, such as an MP3 player-on-a-chip integrated circuit.

In general, the ANC techniques of the present invention measure ambient acoustic events (as opposed to the output of speaker SPKR and/or the near-end speech) impinging on reference microphone R, and by also measuring the same ambient acoustic events impinging on error microphone E, the ANC processing circuits of illustrated wireless telephone 10 adapt an anti-noise signal generated from the output of reference microphone R to have a characteristic that minimizes the amplitude of the ambient acoustic events at error microphone E. Since acoustic path P(z) extends from reference microphone R to error microphone E, the ANC circuits are essentially estimating acoustic path P(z) combined with removing effects of an electro-acoustic path S(z) that represents the response of the audio output circuits of CODEC IC 20 and the acoustic/electric transfer function of speaker SPKR including the coupling between speaker SPKR and error microphone E in the particular acoustic environment, which is affected by the proximity and structure of ear 5 and other physical objects and human head structures that may be in proximity to wireless telephone 10, when wireless telephone is not firmly pressed to ear 5. While the illustrated wireless telephone 10 includes a two microphone ANC system with a third near speech microphone NS, some aspects of the present invention may be practiced in a system that does not include separate error and reference microphones, or a wireless telephone uses near speech microphone NS to perform the function of the reference microphone R. Also, in personal audio devices designed only for audio playback, near speech microphone NS will generally not be included, and the near-speech signal paths in the circuits described in further detail below can be omitted, without changing the scope of the invention.

Figure 2:
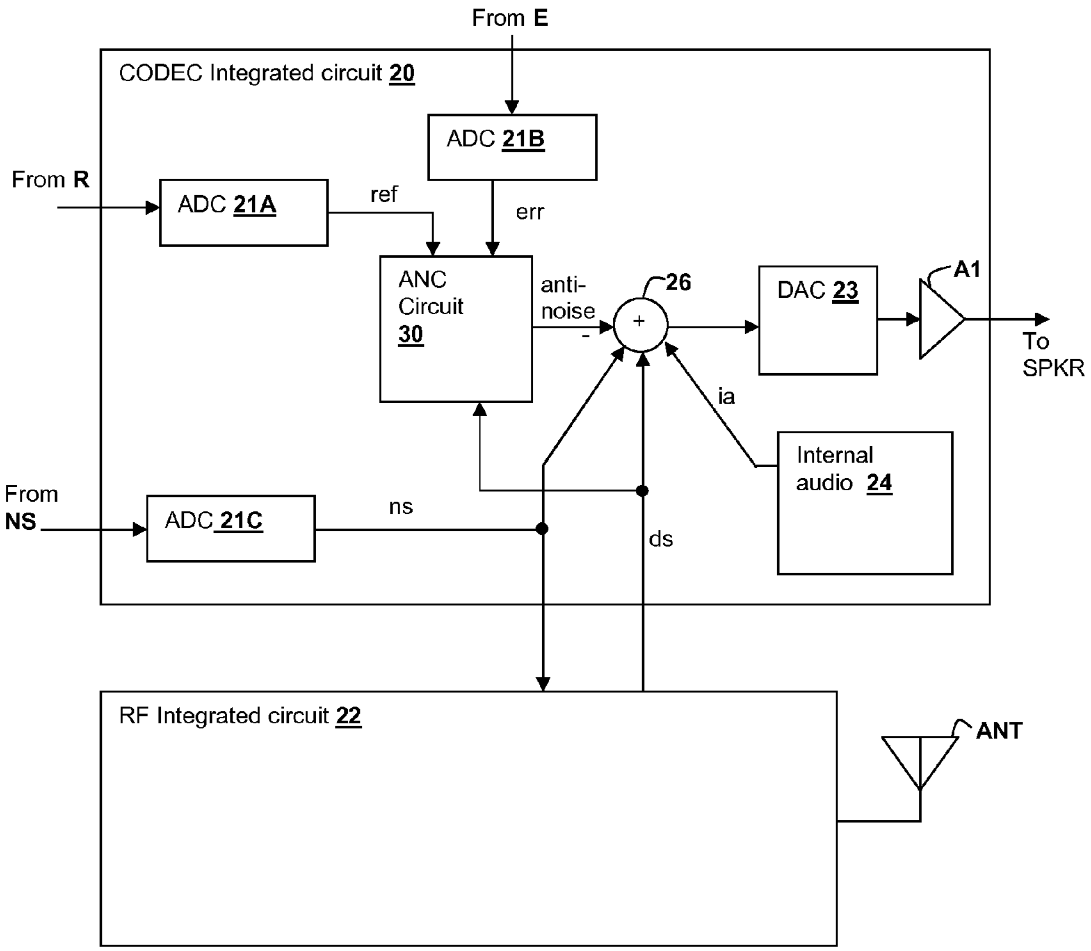
FIG. 2 is a block diagram of circuits within wireless telephone 10 in accordance with an embodiment of the present invention.

Referring now to FIG. 2, circuits within wireless telephone 10 are shown in a block diagram. CODEC integrated circuit 20 includes an analog-to-digital converter (ADC) 21A for receiving the reference microphone signal and generating a digital representation ref of the reference microphone signal, an ADC 21B for receiving the error microphone signal and generating a digital representation err of the error microphone signal, and an ADC 21C for receiving the near speech microphone signal and generating a digital representation ns of the error microphone signal. CODEC IC 20 generates an output for driving speaker SPKR from an amplifier A1, which amplifies the output of a digital-to-analog converter (DAC) 23 that receives the output of a combiner 26. Combiner 26 combines audio signals from internal audio sources 24, the anti-noise signal generated by ANC circuit 30, which by convention has the same polarity as the noise in reference microphone signal ref and is therefore subtracted by combiner 26, a portion of near speech signal ns so that the user of wireless telephone 10 hears their own voice in proper relation to downlink speech ds, which is received from radio frequency (RF) integrated circuit 22 and is also combined by combiner 26. Near speech signal ns is also provided to RF integrated circuit 22 and is transmitted as uplink speech to the service provider via antenna ANT.

Figure 3:
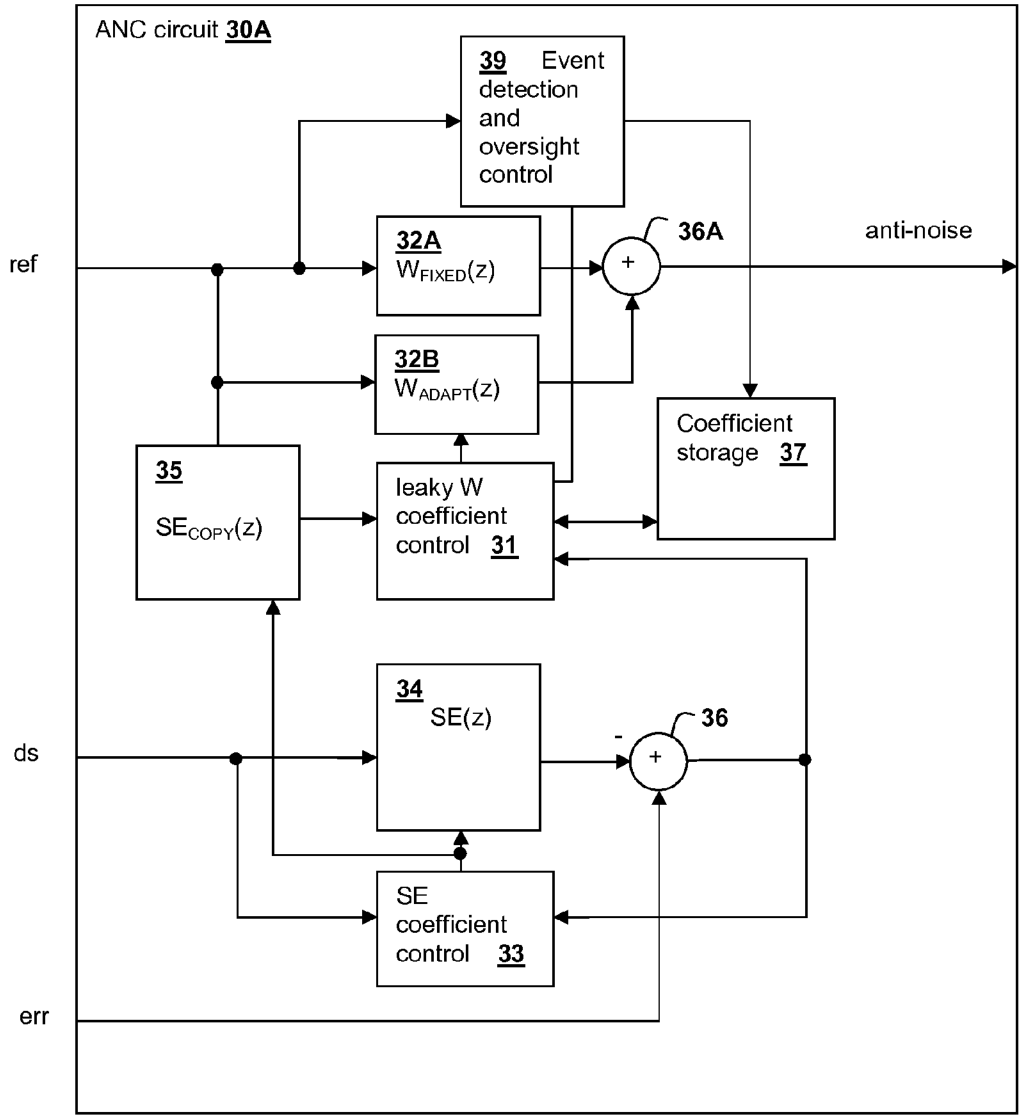
FIG. 3 is a block diagram depicting signal processing circuits and functional blocks within an ANC circuit 30A that can be used to implement ANC circuit 30 of FIG. 2 in accordance with an embodiment of the present invention.

Referring now to FIG. 3, details are shown of an ANC circuit 30A, in accordance with an embodiment of the present invention, that may be used to implement ANC circuit 30 of FIG. 2. A fixed filter portion 32A has a response $W_{FIXED}(z)$ and an adaptive filter portion 32B having a response $W_{ADAPT}(z)$ are coupled in parallel to receive reference microphone signal ref and under ideal circumstances, adaptive filter portion 32B adapts its transfer function $W_{ADAPT}(z)$ so that $W_{ADAPT}(z)+W_{FIXED}(z)$ is equal to P(z)/S(z) to generate the correct anti-noise signal, which is provided to an output combiner 36A that combines the anti-noise signal with the audio to be reproduced by the transducer, as exemplified by combiner 26 of FIG. 2. The coefficients of adaptive filter portion 32B are controlled by a leaky W coefficient control block 31 that uses a correlation of two signals to determine the response of adaptive filter portion 32B, which generally minimizes the error, in a least-mean squares sense, between those components of reference microphone signal ref present in error microphone signal err. The signals compared by leaky W coefficient control block 31 are the reference microphone signal ref as shaped by a copy of an estimate of the response of path S(z) provided by filter 35 and another signal that includes error microphone signal err. By transforming reference microphone signal ref with a copy of the estimate of the response of path S(z), $SE_{COPY}(z)$, and minimizing the difference between the resultant signal and error microphone signal err, adaptive filter portion 32B adapts to the desired response $W_{ADAPT}(z)=P(z)/S(z)-W_{FIXED}(z)$.

Leaky W coefficient control block 31 is leaky in that response $W_{ADAPT}(z)$ normalizes to flat or otherwise predetermined response over time when no error input is provided to cause leaky LMS coefficient controller 31 to adapt. A flat response, $W_{ADAPT}(z)=0$, allows response $W_{FIXED}(z)$ to be set to a desired default, i.e., start-up or reset, response so that the total response of fixed filter portion 32A and adaptive filter portion 32B tends toward response $W_{FIXED}(z)$ over time. Providing a leaky response adaptation prevents long-term instabilities that might arise under certain environmental conditions, and in general makes the system more robust against particular sensitivities of the ANC response. An exemplary leakage control equation is given by:

$$W_{k+1}=(1-\Gamma)\cdot W_k+\mu\cdot e_k\cdot X_k$$

where $\mu=2^{-normalized\_stepsize}$ and normalized_stepsize is a control value to control the step between each increment of k, $\Gamma=2^{-normalized\_leakage}$, where normalized_leakage is a control value that determines the amount of leakage, $e_k$ is the magnitude of the error signal, $X_k$ is the magnitude of the reference microphone signal ref after filtering by the secondary path estimate copy provided by the response of filter 35, $W_k$ is the starting magnitude of the amplitude response of adaptive filter portion 32B and where $W_{k+1}$ are the updated coefficients of adaptive filter portion 32B. The leakage of leakage of LMS coefficient controller 31 may be increased when events are detected that indicate that the response of adaptive filter portion 32B may assume an incorrect value, e.g., the leakage of LMS coefficient controller 31 can be increased when near-end speech is detected, so that the anti-noise signal is eventually generated from the fixed response, until the near-end speech has ended and the adaptive filter can again adapt to cancel the ambient environment at the listener's ear.

The step size implemented by LMS coefficient controller 31 may have a fixed or selectable rate, as well as a fixed or selectable degree of leakage, as mentioned above. If the leakage is set to restore the response of adaptive filter portion 32B to a zero response, then the response of fixed filter portion 32A with respect to the maximum possible response variation of the adaptive filter portion 32B determines the degree to which the leakage can affect the anti-noise signal generation. The response of fixed filter portion 32A may also be made selectable, such that although the response of fixed filter portion 32A is not dynamically adapted as for adaptive filter portion 32B, the response of fixed filter portion 32A may be selected for particular environments, particular devices, particular users or in response to detection of particular audio events. To customize the device, historical values of the combined response of adaptive filter portion 32B and fixed filter portion 32A may be applied as the response to fixed filter portion 32A, at start-up or in response to an audio event, so that adaptive filter portion 32B only needs to adapt to vary the combined response from that of the historic response, which may be selected from among multiple historic values. Similarly, the initial response of the adaptive filter portion 32B may also be selected, alone or in combination with the selection of the initial response of the adaptive filter portion 32B. A coefficient storage 37 is coupled to LMS coefficient controller 31 to record and subsequently select historical and/or predetermined coefficient sets, which may be selected in response to an event detection block 39 detecting an ambient audio event.

In addition to error microphone signal err, the signal compared to the output of filter 35 by W coefficient control block 31 includes an inverted amount of downlink audio signal ds that has been processed by filter response SE(z), of which response $SE_{COPY}(z)$ is a copy. By injecting an inverted amount of downlink audio signal ds, adaptive portion filter 32B is prevented from adapting to the relatively large amount of downlink audio present in error microphone signal err, and by transforming that inverted copy of downlink audio signal ds with the estimate of the response of path S(z), the downlink audio that is removed from error microphone signal err before comparison should match the expected version of downlink audio signal ds reproduced at error microphone signal err, since the electrical and acoustical path of S(z) is the path taken by downlink audio signal ds to arrive at error microphone E. Filter 35 is not an adaptive filter, per se, but has an adjustable response that is tuned to match the response of an adaptive filter 34 that is used to estimate the response of acoustical path S(z), so that the response of filter 35 tracks the adapting of adaptive filter 34.

To implement the above, adaptive filter 34 has coefficients controlled by SE coefficient control block 33, which compares downlink audio signal ds and error microphone signal err after removal of the above-described filtered downlink audio signal ds, that has been filtered by adaptive filter 34 to represent the expected downlink audio delivered to error microphone E, and which is removed from the output of adaptive filter 34 by a combiner 36. SE coefficient control block 33 correlates the actual downlink speech signal ds with the components of downlink audio signal ds that are present in error microphone signal err. Adaptive filter 34 is thereby adapted to generate a signal from downlink audio signal ds, that when subtracted from error microphone signal err, contains the content of error microphone signal err that is not due to downlink audio signal ds.

Figure 4:
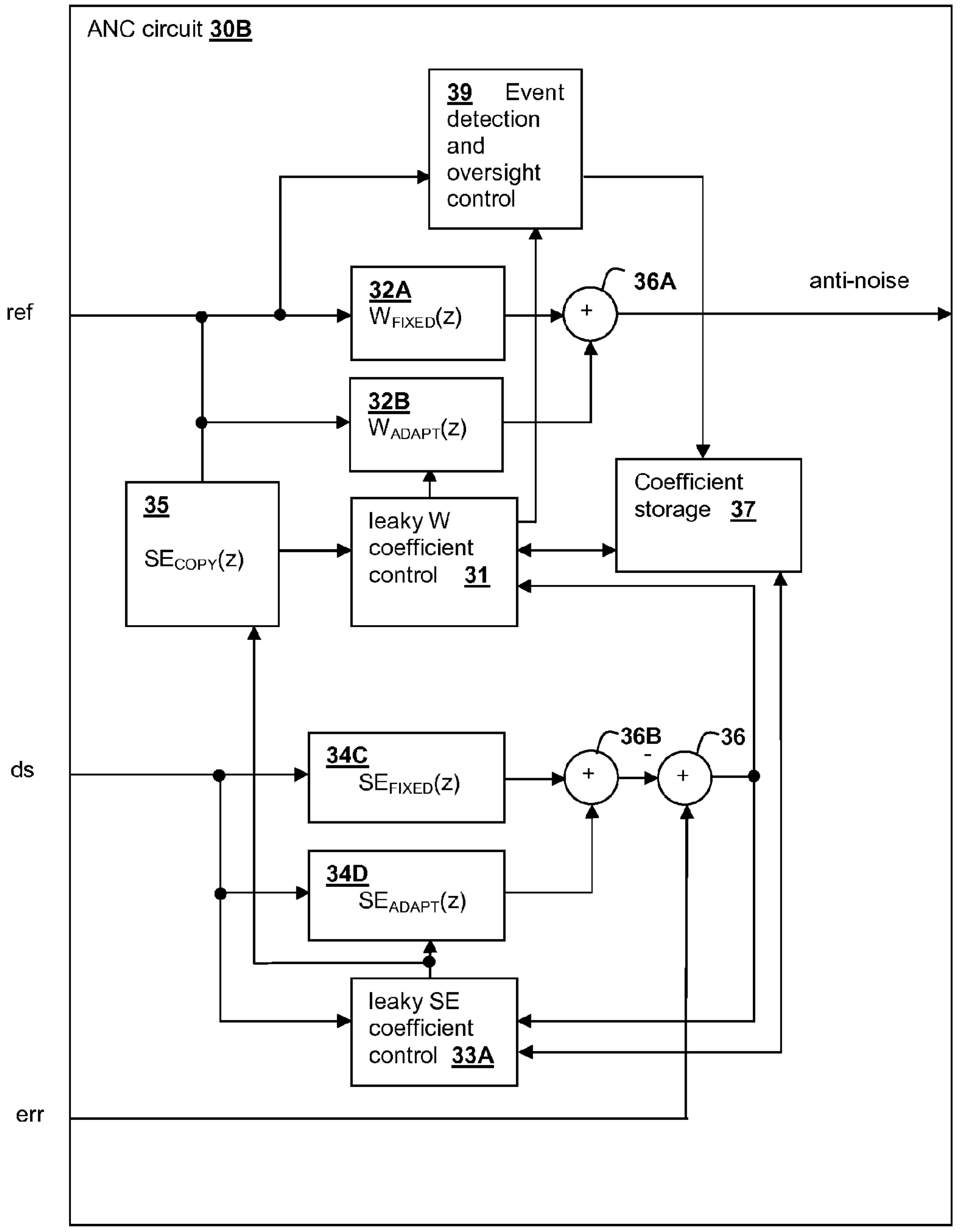
FIG. 4 is a block diagram depicting signal processing circuits and functional blocks within an ANC circuit 30B that can be used to implement ANC circuit 30 of FIG. 2 in accordance with another embodiment of the present invention.

Referring now to FIG. 4, details are shown of another ANC circuit 30B, in accordance with another embodiment of the present invention, that may be used to implement ANC circuit 30 of FIG. 2. The operation and structure of ANC circuit 30B is similar to that of ANC circuit 30A of FIG. 3, so only differences between them will be described in detail below. ANC circuit 30B includes a secondary path filter that is also split into two portions: A fixed filter portion 34C has a response $SE_{FIXED}(z)$ and an adaptive filter portion 34D having a response $SE_{ADAPT}(z)$ are coupled in parallel to filter downlink audio signal ds for generation of the error signal as described above. Adaptive filter portion 34D has coefficients controlled by a leaky SE coefficient control block 33A, which has a leakage characteristic similar to that described above with reference to FIG. 3, although leaky SE coefficient control block 33A may have a different time constant and leakage amount or step size from that of leaky W coefficient control block 31. While not separately illustrated herein, the present invention includes embodiments in which only the secondary path response is partitioned into fixed and adaptive portions. In such embodiments, fixed filter portion 34C and adaptive filter portion 34D are provided, but fixed filter portion 32A and adaptive filter portion 32B are replaced by a single non-partitioned adaptive filter that filters reference microphone signal ref to generate the anti-noise signal.

Figure 5:
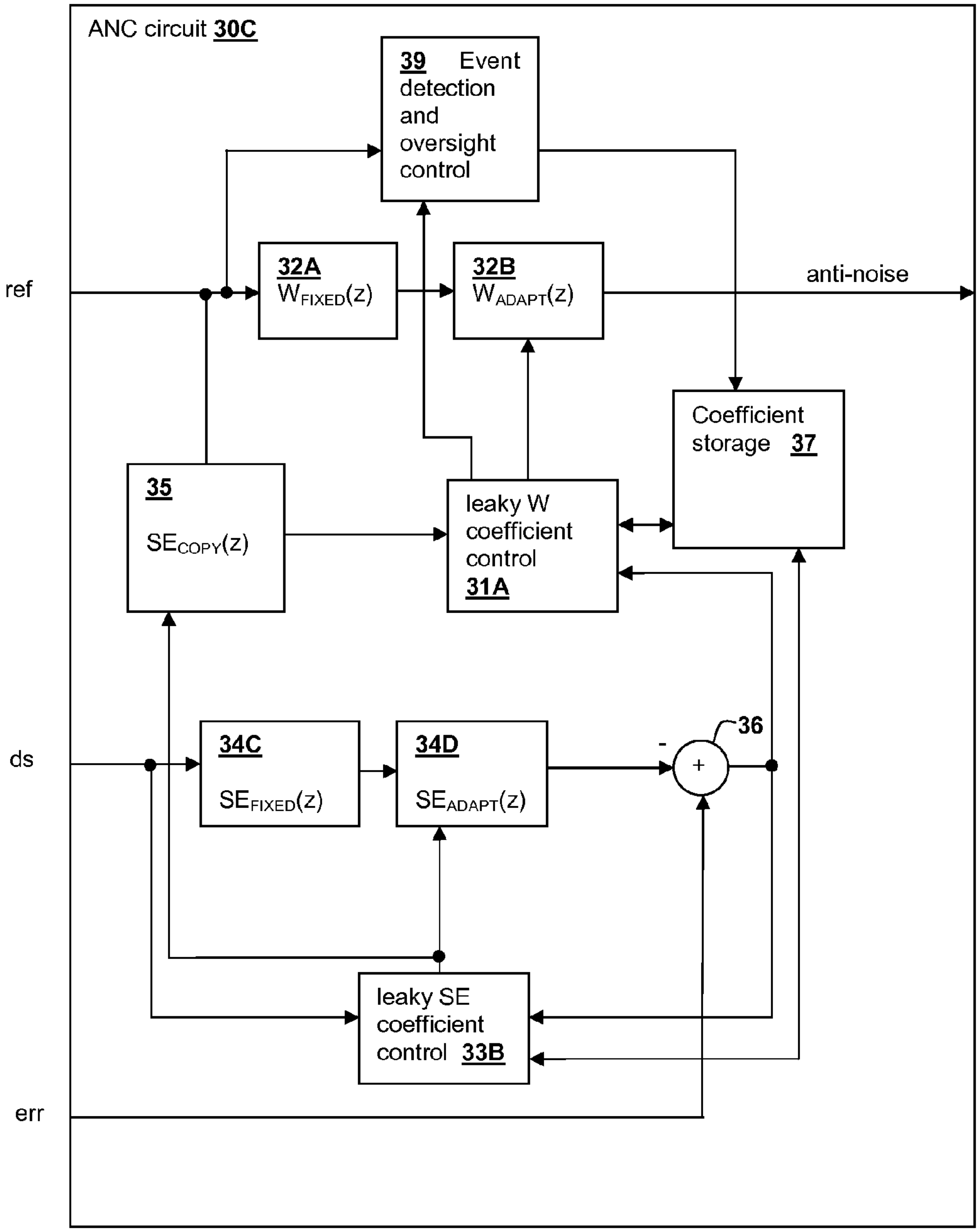
FIG. 5 is a block diagram depicting signal processing circuits and functional blocks within an ANC circuit 30C that can be used to implement ANC circuit 30 of FIG. 2 in accordance with yet another embodiment of the present invention.

Referring now to FIG. 5, details are shown of another ANC circuit 30C, in accordance with another embodiment of the present invention, that may be used to implement ANC circuit 30 of FIG. 2. The operation and structure of ANC circuit 30C is similar to that of ANC circuit 30B of FIG. 4, so only differences between them will be described in detail below. In each of the partitioned filters formed by filter portions 32A, 32B and by filter portions 34C, 34D, the filter portions are cascaded in a serial connection, so that, in the depicted embodiment, the adaptive response of filter portions 32B and 34D are superimposed on the fixed responses of filter portions 32A and 34C, respectively. Therefore, leaky coefficient control blocks 31A and 33B differ from their counterparts in FIG. 4, in that the responses are multiplied rather than added. Any combination of series or parallel connection of fixed/variable filter portions on either the secondary path or the direct path between reference microphone signal ref and the anti-noise signal may be implemented in one or both of the secondary and direct paths, in accordance with different embodiments of the invention.

Figure 6:
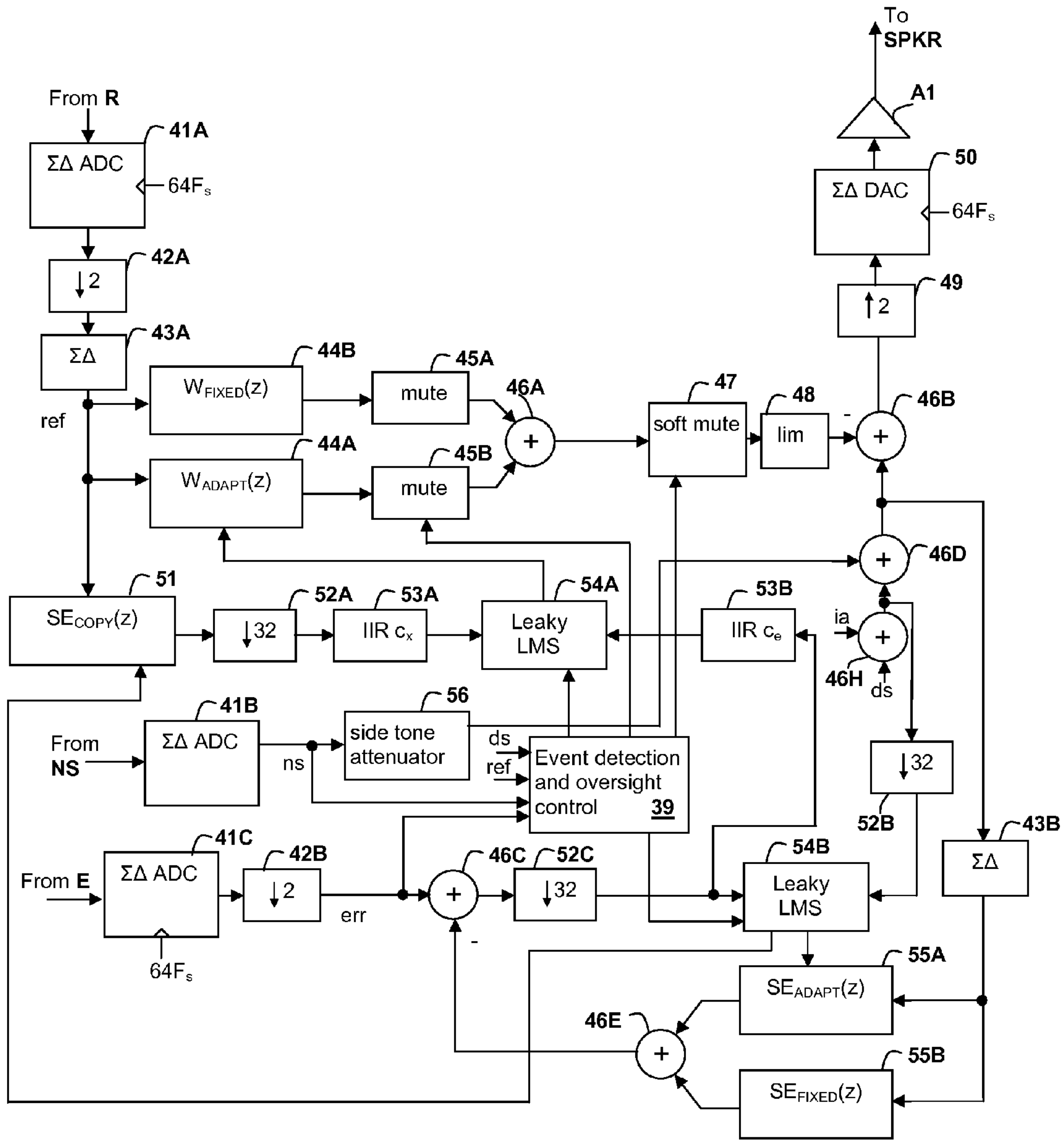
FIG. 6 is a block diagram depicting signal processing circuits and functional blocks within an integrated circuit in accordance with an embodiment of the present invention.

Referring now to FIG. 6, a block diagram of an ANC system is shown for illustrating ANC techniques in accordance with an embodiment of the invention, as may be implemented within CODEC integrated circuit 20. Reference microphone signal ref is generated by a delta-sigma ADC 41A that operates at 64 times oversampling and the output of which is decimated by a factor of two by a decimator 42A to yield a 32 times oversampled signal. A delta-sigma shaper 43A spreads the energy of images outside of bands in which a resultant response of a parallel pair of filter stages 44A and 44B will have significant response. Filter stage 44B has a fixed response $W_{FIXED}(z)$ that is generally predetermined to provide a starting point at the estimate of P(z)/S(z) for the particular design of wireless telephone 10 for a typical user. An adaptive portion $W_{ADAPT}(z)$ of the response of the estimate of P(z)/S(z) is provided by adaptive filter stage 44A, which is controlled by a leaky least-means-squared (LMS) coefficient controller 54A.

In the system depicted in FIG. 6, the reference microphone signal is filtered by a copy $SE_{COPY}(z)$ of the estimate of the response of path S(z), by a filter 51 that has a response $SE_{COPY}(z)$, the output of which is decimated by a factor of 32 by a decimator 52A to yield a baseband audio signal that is provided, through an infinite impulse response (IIR) filter 53A to leaky LMS 54A. Filter 51 is not an adaptive filter, per se, but has an adjustable response that is tuned to match the combined response of filters 55A and 55B, so that the response of filter 51 tracks the adapting of SE(z).The error microphone signal err is generated by a delta-sigma ADC 41C that operates at 64 times oversampling and the output of which is decimated by a factor of two by a decimator 42B to yield a 32 times oversampled signal. As in the systems of FIG. 3 and FIG. 4, an amount of downlink audio ds that has been filtered by an adaptive filter to apply response S(z) is removed from error microphone signal err by a combiner 46C, the output of which is decimated by a factor of 32 by a decimator 52C to yield a baseband audio signal that is provided, through an infinite impulse response (IIR) filter 53B to leaky LMS 54A. Response S(z) is produced by another parallel set of filter stages 55A and 55B, one of which, filter stage 55B has fixed response $SE_{FIXED}(z)$, and the other of which, filter stage 55A has an adaptive response $SE_{ADAPT}(z)$ controlled by leaky LMS coefficient controller MB. The outputs of filter stages 55A and 55B are combined by a combiner 46E. Similar to the implementation of filter response W(z) described above, response $SE_{FIXED}(z)$ is generally a predetermined response known to provide a suitable starting point under various operating conditions for electrical/acoustical path S(z). Filter 51 is a copy of adaptive filter 55A/55B, but is not itself an adaptive filter, i.e., filter 51 does not separately adapt in response to its own output, and filter 51 can be implemented using a single stage or a dual stage. A separate control value is provided in the system of FIG. 6 to control the response of filter 51, which is shown as a single filter stage. However, filter 51 could alternatively be implemented using two parallel stages and the same control value used to control adaptive filter stage 55A could then be used to control the adjustable filter portion in the implementation of filter 51. The inputs to leaky LMS control block 54B are also at baseband, provided by decimating a combination of downlink audio signal ds and internal audio ia, generated by a combiner 46H, by a decimator 52B that decimates by a factor of 32, and another input is provided by decimating the output of a combiner 46C that has removed the signal generated from the combined outputs of adaptive filter stage 55A and filter stage 55B that are combined by another combiner 46E. The output of combiner 46C represents error microphone signal err with the components due to downlink audio signal ds removed, which is provided to LMS control block 54B after decimation by decimator 52C. The other input to LMS control block 54B is the baseband signal produced by decimator 52B.

The above arrangement of baseband and oversampled signaling provides for simplified control and reduced power consumed in the adaptive control blocks, such as leaky LMS controllers MA and 54B, while providing the tap flexibility afforded by implementing adaptive filter stages 44A-44B, 55A-55B and filter 51 at the oversampled rates. The remainder of the system of FIG. 6 includes combiner 46H that combines downlink audio ds with internal audio ia, the output of which is provided to the input of a combiner 46D that adds a portion of near-end microphone signal ns that has been generated by sigma-delta ADC 41B and filtered by a sidetone attenuator 56 to prevent feedback conditions. The output of combiner 46D is shaped by a sigma-delta shaper 43B that provides inputs to filter stages 55A and 55B that has been shaped to shift images outside of bands where filter stages 55A and 55B will have significant response In accordance with an embodiment of the invention, the output of combiner 46D is also combined with the output of adaptive filter stages 44A-44B that have been processed by a control chain that includes a corresponding hard mute block 45A, 45B for each of the filter stages, a combiner 46A that combines the outputs of hard mute blocks 45A, 45B, a soft mute 47 and then a soft limiter 48 to produce the anti-noise signal that is subtracted by a combiner 46B with the source audio output of combiner 46D. The output of combiner 46B is interpolated up by a factor of two by an interpolator 49 and then reproduced by a sigma-delta DAC 50 operated at the 64× oversampling rate. The output of DAC 50 is provided to amplifier A1, which generates the signal delivered to speaker SPKR.

Each or some of the elements in the system of FIG. 6, as well as in the exemplary circuits of FIG. 2, FIG. 3 and FIG. 4, can be implemented directly in logic, or by a processor such as a digital signal processing (DSP) core executing program instructions that perform operations such as the adaptive filtering and LMS coefficient computations. While the DAC and ADC stages are generally implemented with dedicated mixed-signal circuits, the architecture of the ANC system of the present invention will generally lend itself to a hybrid approach in which logic may be, for example, used in the highly oversampled sections of the design, while program code or microcode-driven processing elements are chosen for the more complex, but lower rate operations such as computing the taps for the adaptive filters and/or responding to detected events such as those described herein.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. A personal audio device, comprising:

a personal audio device housing;

a transducer mounted on the housing for reproducing an audio signal including both source audio for playback to a listener and an anti-noise signal for countering the effects of ambient audio sounds in an acoustic output of the transducer;

a reference microphone mounted on the housing for providing a reference microphone signal indicative of the ambient audio sounds; and a processing circuit that generates the anti-noise signal from the reference microphone signal to reduce the presence of the ambient audio sounds heard by the listener, wherein the processing circuit implements a partitioned filter that controls the generation of the anti-noise signal, wherein the filter is partitioned into a first filter portion having a fixed frequency response that is combined with a variable frequency response of a second filter portion, wherein the first filter portion and the second filter portion are coupled in parallel and receive identical inputs, wherein the processing circuit sums an output of the first filter portion and an output of the second filter portion to generate the anti-noise signal, and wherein the processing circuit shapes the spectrum of the anti-noise signal in conformity with the reference microphone signal to minimize the ambient audio sounds heard by the listener.

2. The personal audio device of claim 1, wherein the partitioned filter receives the reference microphone signal and generates the anti-noise signal by filtering the reference microphone signal.

3. The personal audio device of claim 1, further comprising an error microphone mounted on the housing in proximity to the transducer for providing an error microphone signal indicative of the acoustic output of the transducer and the ambient audio sounds at the transducer, and wherein the processing circuit implements an adaptive filter that generates the anti-noise signal in conformity with the error microphone signal and the reference microphone signal by adapting the variable frequency response of the second filter portion to minimize the ambient audio sounds at the error microphone, and wherein the partitioned filter is a secondary path filter having a secondary path response that shapes the source audio and a combiner that removes the source audio from the error microphone signal to provide an error signal indicative of the combined anti-noise and ambient audio sounds delivered to the listener, wherein the processing circuit adapts the variable response of the second filter to minimize components of the error signal that are correlated with an output of another filter that applies a copy of the secondary path response to the reference microphone signal.

4. The personal audio device of claim 3, wherein the processing circuit further implements a third filter that receives the reference microphone signal and generates the anti-noise signal by filtering the reference microphone signal, wherein the third filter is partitioned into a third filter portion having another fixed frequency response that is combined with another variable frequency response of a fourth filter portion.

5. The personal audio device of claim 1, wherein an adaptive control of the variable frequency response of the second filter portion has a leakage characteristic that restores the response of the partitioned filter to a predetermined response at a particular rate of change.

6. The personal audio device of claim 5, wherein the leakage characteristic restores the response of the partitioned filter to the fixed frequency response of the first filter portion.

7. The personal audio device of claim 1, wherein the fixed frequency response of the first filter portion is selectable from among multiple predetermined frequency responses.

8. The personal audio device of claim 7, wherein at least one of the multiple predetermined frequency responses is an historic frequency response of the partitioned filter representing a combination of the fixed frequency response of the first filter portion and a historic frequency response of the second filter portion, wherein the processing circuit selects the at least one of the multiple predetermined frequency responses to initialize the combined response of the partitioned filter to a previously adapted-to state.

9. The personal audio device of claim 7, wherein the processing circuit selects the fixed frequency response of the first filter in conformity with a heuristic or a detected environmental condition.

10. The personal audio device of claim 1, wherein an initial value of the variable frequency response of the second filter portion is selectable from among multiple predetermined frequency responses.

11. The personal audio device of claim 10, wherein at least one of the multiple predetermined frequency responses is an historic frequency response of the second filter portion, wherein the processing circuit selects the at least one of the multiple predetermined frequency responses to initialize the variable frequency response of the second filter portion to a previously adapted-to state.

12. The personal audio device of claim 10, wherein the processing circuit selects the initial value of the variable frequency response of the second filter portion in conformity with a heuristic or a detected environmental condition.

13. A method of canceling ambient audio sounds in the proximity of a transducer of a personal audio device, the method comprising:

first measuring ambient audio sounds with a reference microphone to produce a reference microphone signal;

adaptively generating an anti-noise signal for countering the effects of ambient audio sounds at an acoustic output of the transducer, to shape the spectrum of the anti-noise signal in conformity with the reference microphone signal to minimize the ambient audio sounds heard by the listener, wherein the adaptively generating controls the generation of the anti-noise signal using a combined response of a first fixed filter response and a second variable filter response, further comprising combining an output of the first fixed filter response and an output of the second variable filter response to yield a combined output, and further comprising cascading the first fixed filter response and the second variable filter response to yield a combined output; and combining the anti-noise signal with a source audio signal to generate an audio signal provided to the transducer.

14. The method of claim 13, wherein the first fixed filter response and the second fixed filter response receive the reference microphone signal and generate the anti-noise signal by filtering the reference microphone signal.

15. The method of claim 13, further comprising second measuring an output of the transducer and the ambient audio sounds at the transducer with an error microphone to produce an error microphone signal, wherein the adaptively generating adjusts the second variable filter response in conformity with the error microphone signal and the reference microphone signal by adapting the variable response to minimize the ambient audio sounds at the error microphone, and wherein the combined response of the first fixed filter response and the second adaptive filter response implements a secondary path response that shapes the source audio to generate shaped source audio, and wherein the method further comprises:

removing the shaped source audio from the error microphone signal to provide an error signal indicative of the combined anti-noise and ambient audio sounds delivered to the listener; and filtering the reference microphone signal with a copy of the secondary path response to generate a shaped reference microphone signal, and wherein the adaptively generating adjusts the second variable filter response to minimize components of the error signal that are correlated with the shaped reference microphone signal.

16. The method of claim 15, wherein the adaptively generating generates the anti-noise signal by:

first filtering the reference microphone signal with a third fixed filter response;

second filtering the reference microphone signal with a fourth variable filter response; and combining a result of the first filtering and a result of the second filtering to generate the anti-noise signal, wherein the adaptively generating further adjusts the fourth variable filter response to minimize the ambient audio sounds at the error microphone.

17. The method of claim 13, wherein the adaptively generating controls the variable response of the second filter portion with a leakage characteristic that restores the response of the partitioned filter to a predetermined response at a particular rate of change.

18. The method of claim 17, wherein the leakage characteristic restores the response of the partitioned filter to the first fixed filter response.

19. The method of claim 13, further comprising selecting the first fixed filter response from among multiple predetermined frequency responses.

20. The method of claim 19, wherein at least one of the multiple predetermined frequency responses is an historic frequency response of the partitioned filter representing a combination of the first fixed filter response and an historic of the second variable filter response, wherein the selecting selects the at least one of the multiple predetermined frequency responses to initialize a frequency response of the combined filter response to a previously adapted-to state.

21. The method of claim 19, wherein the processing circuit selects the fixed frequency response of the first filter in conformity with a heuristic or a detected environmental condition.

22. The method of claim 13, further comprising selecting an initial value of the second variable filter response from among multiple predetermined frequency responses.

23. The method of claim 22, wherein at least one of the multiple predetermined frequency responses is an historic value of the second variable filter response, wherein the selecting selects the at least one of the multiple predetermined frequency responses to initialize the second variable filter response to a previously adapted-to state.

24. The method of claim 22, wherein the selecting selects the initial value of the second variable filter response in conformity with a heuristic or a detected environmental condition.

25. An integrated circuit for implementing at least a portion of a personal audio device, comprising:

an output for providing a signal to a transducer including both source audio for playback to a listener and an anti-noise signal for countering the effects of ambient audio sounds in an acoustic output of the transducer;

a reference microphone input for receiving a reference microphone signal indicative of the ambient audio sounds; and a processing circuit that generates the anti-noise signal from the reference microphone signal to reduce the presence of the ambient audio sounds heard by the listener, wherein the processing circuit implements a partitioned filter that controls the generation of the anti-noise signal, wherein the filter is partitioned into a first filter portion having a fixed frequency response that is combined with a variable frequency response of a second filter portion, wherein the first filter portion and the second filter portion are coupled in parallel and receive identical inputs, wherein the processing circuit sums an output of the first filter portion and an output of the second filter portion to generate the anti-noise signal, and wherein the processing circuit shapes the spectrum of the anti-noise signal in conformity with the reference microphone signal to minimize the ambient audio sounds heard by the listener.

26. The integrated circuit of claim 25, wherein the partitioned filter receives the reference microphone signal and generates the anti-noise signal by filtering the reference microphone signal.

27. The integrated circuit of claim 25, further comprising an error microphone input for receiving an error microphone signal indicative of the output of the transducer and the ambient audio sounds at the transducer, and wherein the processing circuit implements an adaptive filter that generates the anti-noise signal in conformity with the error microphone signal and the reference microphone signal by adapting the variable frequency response of the second filter portion to minimize the ambient audio sounds at the error microphone, and wherein the partitioned filter is a secondary path filter having a secondary path response that shapes the source audio and a combiner that removes the source audio from the error microphone signal to provide an error signal indicative of the combined anti-noise and ambient audio sounds delivered to the listener, wherein the processing circuit adapts the variable response of the second filter to minimize components of the error signal that are correlated with an output of another filter that applies a copy of the secondary path response to the reference microphone signal.

28. The integrated circuit of claim 27, wherein the processing circuit further implements a third filter that receives the reference microphone signal and generates the anti-noise signal by filtering the reference microphone signal , wherein the third filter is partitioned into a third filter portion having another fixed frequency response that is combined with another variable frequency response of a fourth filter portion.

29. The integrated circuit of claim 25, wherein an adaptive control of the variable frequency response of the second filter portion has a leakage characteristic that restores the response of the partitioned filter to a predetermined response at a particular rate of change.

30. The integrated circuit of claim 29, wherein the leakage characteristic restores the response of the partitioned filter to the fixed frequency response of the first filter portion.

31. The integrated circuit of claim 25, wherein the fixed frequency response of the first filter portion is selectable from among multiple predetermined frequency responses.

32. The integrated circuit of claim 31, wherein at least one of the multiple predetermined frequency responses is an historic frequency response of the partitioned filter representing a combination of the fixed frequency response of the first filter portion and a historic frequency response of the second filter portion, wherein the processing circuit selects the at least one of the multiple predetermined frequency responses to initialize the combined response of the partitioned filter to a previously adapted-to state.

33. The integrated circuit of claim 31, wherein the processing circuit selects the fixed frequency response of the first filter in conformity with a heuristic or a detected environmental condition.

34. The integrated circuit of claim 25, wherein an initial value of the variable frequency response of the second filter portion is selectable from among multiple predetermined frequency responses.

35. The integrated circuit of claim 34, wherein at least one of the multiple predetermined frequency responses is an historic frequency response of the second filter portion, wherein the processing circuit selects the at least one of the multiple predetermined frequency responses to initialize the variable frequency response of the second filter portion to a previously adapted-to state.

36. The integrated circuit of claim 34, wherein the processing circuit selects the initial value of the variable frequency response of the second filter portion in conformity with a heuristic or a detected environmental condition.

* * * * *